(12) United States Patent
Radivojevic et al.

(10) Patent No.: US 7,868,757 B2
(45) Date of Patent: Jan. 11, 2011

(54) METHOD FOR THE MONITORING OF SLEEP USING AN ELECTRONIC DEVICE

(75) Inventors: Zoran Radivojevic, Helsinki (FI); Jarkko Saunamaki, Vantaa (FI)

(73) Assignee: Nokia Corporation, Espoo (FI)

( * ) Notice: Subject to any disclaimer, the term of this patent is extended or adjusted under 35 U.S.C. 154(b) by 787 days.

(21) Appl. No.: 11/647,429

(22) Filed: Dec. 29, 2006

(65) Prior Publication Data

US 2008/0157956 A1    Jul. 3, 2008

(51) Int. Cl.
*G08B 21/00* (2006.01)
*G08B 23/00* (2006.01)

(52) U.S. Cl. ...................... 340/540; 340/575

(58) Field of Classification Search ......... 340/500–505, 340/539.1, 539.11, 539.12, 540, 575
See application file for complete search history.

(56) References Cited

U.S. PATENT DOCUMENTS

| | | | | |
|---|---|---|---|---|
| 5,689,241 A * | 11/1997 | Clarke et al. | ................. | 340/575 |
| 5,844,488 A * | 12/1998 | Musick | ..................... | 340/573.4 |
| 6,160,478 A * | 12/2000 | Jacobsen et al. | ....... | 340/539.12 |
| 6,392,550 B1 * | 5/2002 | Najor | ......................... | 340/576 |
| 6,791,462 B2 * | 9/2004 | Choi | ............................ | 340/575 |
| 6,823,739 B2 | 11/2004 | Ueno et al. | .................... | 73/717 |
| 6,825,769 B2 * | 11/2004 | Colmenarez et al. | ........ | 340/575 |
| 6,838,994 B2 * | 1/2005 | Gutta et al. | .................. | 340/575 |
| 6,876,964 B1 * | 4/2005 | Shiomi et al. | ................ | 704/202 |
| 6,889,055 B1 * | 5/2005 | Neufeld | ....................... | 455/458 |
| 7,027,358 B1 * | 4/2006 | Esposito et al. | ............... | 368/10 |
| 2002/0080035 A1 * | 6/2002 | Youdenko | ................. | 340/573.1 |
| 2003/0210150 A1 * | 11/2003 | Benedict | ...................... | 340/575 |
| 2004/0034289 A1 | 2/2004 | Teller et al. | .................. | 600/300 |
| 2005/0154330 A1 | 7/2005 | Loree, IV | ..................... | 600/595 |
| 2005/0190065 A1 * | 9/2005 | Ronnholm | ................... | 340/575 |

FOREIGN PATENT DOCUMENTS

| | | |
|---|---|---|
| JP | 5-192315 | 8/1993 |
| JP | 2000-325315 | 11/2000 |
| JP | 2001-258855 | 9/2001 |
| JP | 2004-49271 | 2/2004 |
| JP | EP1393670 A2 * | 3/2004 |

OTHER PUBLICATIONS

Andoh, Hisanori et al., "*Network Health Monitoring System in the Sleep*", SICE Annual Conference, Aug. 4-6, 2004, pp. 1421-1424.

\* cited by examiner

*Primary Examiner*—Jennifer Mehmood
(74) *Attorney, Agent, or Firm*—Ditthavong Mori & Steiner, P.C.

(57) ABSTRACT

The invention relates to a method where sleep sensor signals are obtained to a mobile communication device from sensor devices. The mobile communication device checks the sleep sensor signals for a sleep state transition, determines the type of the sleep state transition, forms control signals based on the type of the sleep state transition and sends the control signals to at least one electronic device.

31 Claims, 3 Drawing Sheets

METHOD FOR THE MONITORING OF SLEEP USING AN ELECTRONIC DEVICE

BACKGROUND OF THE INVENTION

1. Field of the Invention

The invention relates to sleep monitoring. Particularly, the invention relates to a method for the monitoring of sleep using an electronic device.

2. Description of the Related Art

Nowadays mobile phones and palmtop computers, that is, mobile terminals or mobile communication devices are increasingly being used instead of alarm clocks. The alarm works simply by waking up the user at a specified time, which many users find unpleasant. However, present day mobile terminals are equipped with computation power and peripheral device interfacing capabilities that would permit much more sophisticated wakeup and sleep control.

There is also a recent trend to connect household appliances to a local area network together with a personal computer in order to enable a centralized and automatic control of household appliances. The personal computer at home may further be controlled with a mobile terminal via an Internet connection.

Further, there exist available comfortable and unnoticeable sensor devices for the monitoring of sleep. Such sensor devices may be incorporated to a mattress or they may be worn.

Sleep consists of several phases with different depths. There is a delta-phase in which the sleeper is oblivious to normal disturbances. The delta-phase is followed by a Rapid Eye Movements (REM) phase where most dreaming takes place. Sleeper also moves rapidly during the REM sleep. Awakening is easier in the REM phase than in the delta-phase.

It would be beneficial to be able to have a sleep monitoring and wakeup system, which avoids the waking of the sleeper during a period of deep sleep. It would also be beneficial to be able to control household appliances based on the anticipated actual waking time of the sleeper.

SUMMARY OF THE INVENTION

The invention relates to a method comprising: obtaining at least one sleep sensor signal to a mobile communication device; checking said at least one sleep sensor signal for a sleep state transition; determining the type of said sleep state transition;
forming at least one control signal based on the type of said sleep state transition; sending said at least one control signal to at least one electronic device.

The invention relates also to a mobile communication device comprising: a radio receiver configured to receive at least one sleep sensor signal; a processor configured to check said at least one sleep sensor signal for a sleep state transition, to determine the type of said sleep state transition, to form at least one control signal based on the type of said sleep state transition; and a transmitter configured to send said at least one control signal to at least one electronic device.

The invention relates also to a mobile communication device comprising means for obtaining at least one sleep sensor signal to a mobile communication device; means for checking said at least one sleep sensor signal for a sleep state transition; means for determining the type of said sleep state transition; means for forming at least one control signal based on the type of said sleep state transition; and means for sending said at least one control signal to at least one electronic device.

The invention relates also to a system comprising: at least one sleep sensor configured to send at least one sleep sensor signal; and a mobile communication device configured to receive said at least one sleep sensor signal, to check said at least one sleep sensor signal for a sleep state transition, to determine the type of said sleep state transition, to form at least one control signal based on the type of said sleep state transition and to send said at least one control signal to at least one electronic device.

The invention relates also to a computer program comprising code adapted to perform the following steps when executed on a data-processing system: obtaining at least one sleep sensor signal to a mobile communication device; checking said at least one sleep sensor signal for a sleep state transition; determining the type of said sleep state transition; forming at least one control signal based on the type of said sleep state transition; and sending said at least one control signal to at least one electronic device.

The invention relates also to a mobile communication device comprising: a radio receiver configured to receive at least one sleep sensor signal; a microphone configured to receive ambient audio signals; and a processor configured to determine a sleep state or a resting state of a user with said at least one sleep sensor signal, to determine a first disturbing noise pattern in said audio signals, to start the generating of at least one comfort audio pattern in order to alleviate subsequent disturbing noise patterns.

The invention relates also to a system comprising: at least one pressure sensor configured to detect at least one tapping impulse and to form a signal indicative of said at least one tapping impulse; and a mobile communication device configured to receive said signal indicative of said at least one tapping impulse, to determine a function corresponding to said at least one tapping impulse and to request said function.

In one embodiment of the invention, a control entity the mobile communication device is configured to receive said signal indicative of said at least one tapping impulse, to determine a function corresponding to the at least one tapping impulse and to request said function.

In one embodiment of the invention, a control entity in the mobile communication device is configured to request said function from at least one electronic device configured to communicate with said mobile communication device.

In one embodiment of the invention, the control entity in the mobile communication device is configured to determine said function based on the number of tapping impulses closely located in time.

In one embodiment of the invention, the mobile communication device processor executes a control entity configured to determine that the type of said sleep state transition is to sleep state. The control entity is configured to add to said at least one control signal a request to stop or diminish a function prone to disturb sleep.

In one embodiment of the invention, the mobile communication device processor executes a control entity configured to determine that the type of said sleep state transition is to awake, that is, to a state indicating awake, and to add to said at least one control signal a request to start or increase a function. The function is, for example, to put on lighting, to start a coffee maker and to increase air conditioning.

In one embodiment of the invention, the mobile communication device processor executes a control entity configured to determining a time window for the awakening of a person, to determine that the type of said sleep state transition is to the Rapid Eye Movements state, to reach the start of said time window and to delaying a wakeup function in said mobile communication device until a predetermined time is spent in the Rapid Eye Movements state or the end of said time window has been reached.

In one embodiment of the invention, the mobile communication device processor executes a control entity configured to determine that the type of said sleep state transition is to asleep state and to add to said at least one control signal a request to maintain soporific functions of at least one of said at least one electronic device.

In one embodiment of the invention, the mobile communication device processor executes a control entity configured to determine a time window for the awakening of a person, to determine a type of sleep, to determine the reaching of the start of said time window and to adjust a wakeup entity in said mobile communication device based on the type of the person's sleep. The mobile communication device comprising a wakeup entity configured to start at least one wakeup function based on a signal from said control entity.

In one embodiment of the invention, the receiver comprises a short-range radio receiver and the transmitter comprises a radio transmitter.

In one embodiment of the invention, the pressure sensor is adjusted to receive one or more tapping control signals. The tapping control signals may control function of the sleep state transition.

In one embodiment of the invention, the mobile device has also a microphone to monitor environmental, that is, ambient noise. The environmental noise is checked by the control entity in the mobile device. The control entity may use audio output via loudspeaker or headsets to generate a comforting noise, in other words, a voice of low disturbance in order to cover potentially disturbing noise peaks and patterns from the environment. The control entity may also issue a request to an external audio appliance to generate the comforting noise. Additionally, the control entity monitors also sleep sensor signals during the presence of the environmental noise and the comfort noise and the comfort noise may be further adjusted based on the detection of possible sleep disturbance indications. If a sleeper uses head sets also a noise cancellation signal maybe created.

In one embodiment of the invention, said at least one of said at least one electronic device comprises a domestic appliance.

In one embodiment of the invention, the electronic device comprises electronic device comprises at least one of a lighting control device, a radio, a media center, an air conditioning system and noise cancellation device.

In one embodiment of the invention, the sleep sensor signal is formed in at least one sleep sensor.

In one embodiment of the invention, the mobile communication device receives said at least one sleep sensor signal from said at least one sleep sensor via a short-range radio connection.

In one embodiment of the invention, said at least one sleep sensor comprises a wearable band further comprising an accelerometer.

In one embodiment of the invention, said at least one sleep sensor comprises a pressure sensor.

In one embodiment of the invention, the mobile communication device comprises a cellular telephone or a wireless local area network terminal.

In one embodiment of the invention, an external electric switch is triggered for home appliances to improve sleeping commodity and comfort. Such systems can control an air conditioning system, TV/Radio Off/On, open a window to get fresh air in the morning, turn ON/OFF a coffee maker, etc.

The exact conditions for the switch can be defined by user e.g. trigger when a person has fallen asleep and/or entered on a certain level of sleep etc.

In one embodiment of the invention, mobile communication device has alarm which gently moves user from a deep sleep to light sleep by using audio visual means at phone. In practice the user can adjust an adaptive wake up protocol driven by the current phase/level of the sleep i.e. different phases has different wake up methods by audio/video or other means.

In one embodiment of the invention, the mobile communication device provides an alarm by which user awakes slowly just by listening voice of the sleep pattern report at phone. If the voice whispers "You have not reached enough of active sleeping", the user has an option to continue sleeping.

In one embodiment of the invention, an auto answer at the mobile communication device is synchronized with the sleeping pattern, which provides that incoming calls are automatically answered by saying "user is sleeping at the moment and suggest to call latter approximately after N hours, the value N being adjustable, when user is expected to wake up. If the caller is seriously keeping on the line the phone may start belling after 2 minutes.

In one embodiment of the invention, the mobile communication device provides an active sleep alarm to which the user enters information for wakeup after N hours of the active sleep, the value N being configurable for the user.

In one embodiment of the invention, the mobile communication device provides a jet-lag synchronizer service to which the user enters information on date of flight and timezone and return date or connecting flight. The control entity at the mobile communication device starts to adapt to the time zone in destination by decreasing/increasing sleeping time.

In one embodiment of the invention, the mobile communication device provides an optimal sleep time service. Some people need 8 h of sleep, some less. Addition to morning query "rate your sleep", the control entity at phone asks few times during the day how do you feel and in the evening asks how the day went "were your tired". After some days the control entity has calculated the optimum sleeping time. The service can be expanded to full life control: when did you eat, did you eat heavily, did you engage in sports and when etc. in order to find optimum way of life for good sleep. The amount of sleep needed may vary depending what you did during the day.

In one embodiment of the invention, the mobile communication device provides a sleep-calmer service. The control entity recognizes when the person sleeps restless, a self-learning procedure at phone tries different types of sounds/music and finds plus remembers the optimum sound which calms the restless sleeper back to good sleep.

In one embodiment of the invention, the mobile communication device recognizes the awakening and puts phone lights on, if needed to find the phone easier or just to highlight the sleeping room or a way to the toilette.

In one embodiment of the invention, the mobile communication device warns parents/nurse when a child or a patient leaves the bed by sending a message to their mobile communication devices.

In one embodiment of the invention, the mobile communication device provides for control via the sensors so that by tapping a pressure sensor twice music, lighting or television is switched off. The alerting of an incoming call may be deflected as such a tapping is recognized by a pressure sensor.

In one embodiment of the invention, the mobile communication device sleep stages and recognizes when the person fall asleep and turns off the music that was playing at phone.

In one embodiment of the invention, the mobile communication device is configured to send a message to another person when the monitored person is detected to wake up.

In one embodiment of the invention, the user of mobile communication device activates a "Sleep Butler" icon at the phone before going to the bed and selects a certain digital service. The phone is kept in the same room where the user is. The phone is connected through a short-range radio connection or cable to the sensor devices and requires the real time updates from the sensor devices. Depending on the wanted service user may plug into the phone a small gadget which contains IR-LED remote controller and operates as a remote controller towards some other devices AC switch, air conditioner, TV, etc. Notice that such plug and play IR-LED based remote controller can be a universal type (e.g. capable of covering of broaden range of operation). Depending on pre-selected service the real time associate digital service are triggered by the sleep stages and through the phone send a SMS/mail, switch air conditioner/ventilation, turn off/on TV, open a window, etc. Some of the above mentioned services require the IR-LED gadget, some not.

In one embodiment of the invention, said mobile communication device, that is, a mobile terminal is a mobile station in a mobile communication system. In one embodiment of the invention, the mobile communication system comprises at least one of a Global System of Mobile Communications (GSM) network and a Universal Mobile Telephone System (UMTS) network. In one embodiment of the invention, the system comprises a Wireless Local Area Network (WLAN). In one embodiment of the invention, the system comprises also a Worldwide Interoperability for Microwave Access (WiMAX) network. In one embodiment of the invention, the mobile communication device may be, for example, a GSM mobile station or a UMTS mobile station with a dual mode or multimode functionality to support different access types.

In one embodiment of the invention, the computer program is stored on a computer readable medium. The computer readable medium may be a removable memory card, magnetic disk, holographic memory, optical disk or magnetic tape.

The embodiments of the invention described hereinbefore may be used in any combination with each other. Several of the embodiments may be combined together to form a further embodiment of the invention. A method, a mobile communication device, a system or a computer program to which the invention is related may comprise at least one of the embodiments of the invention described hereinbefore.

The benefits of the invention are related to improvements in avoiding disturbing factors while sleeping and to the timely providing of services when the user of the mobile communication device wakes up.

BRIEF DESCRIPTION OF THE DRAWINGS

The accompanying drawings, which are included to provide a further understanding of the invention and constitute a part of this specification, illustrate embodiments of the invention and together with the description help to explain the principles of the invention. In the drawings.

DETAILED DESCRIPTION OF THE EMBODIMENTS

Reference will now be made in detail to the embodiments of the present invention, examples of which are illustrated in the accompanying drawings.

Figure 1:
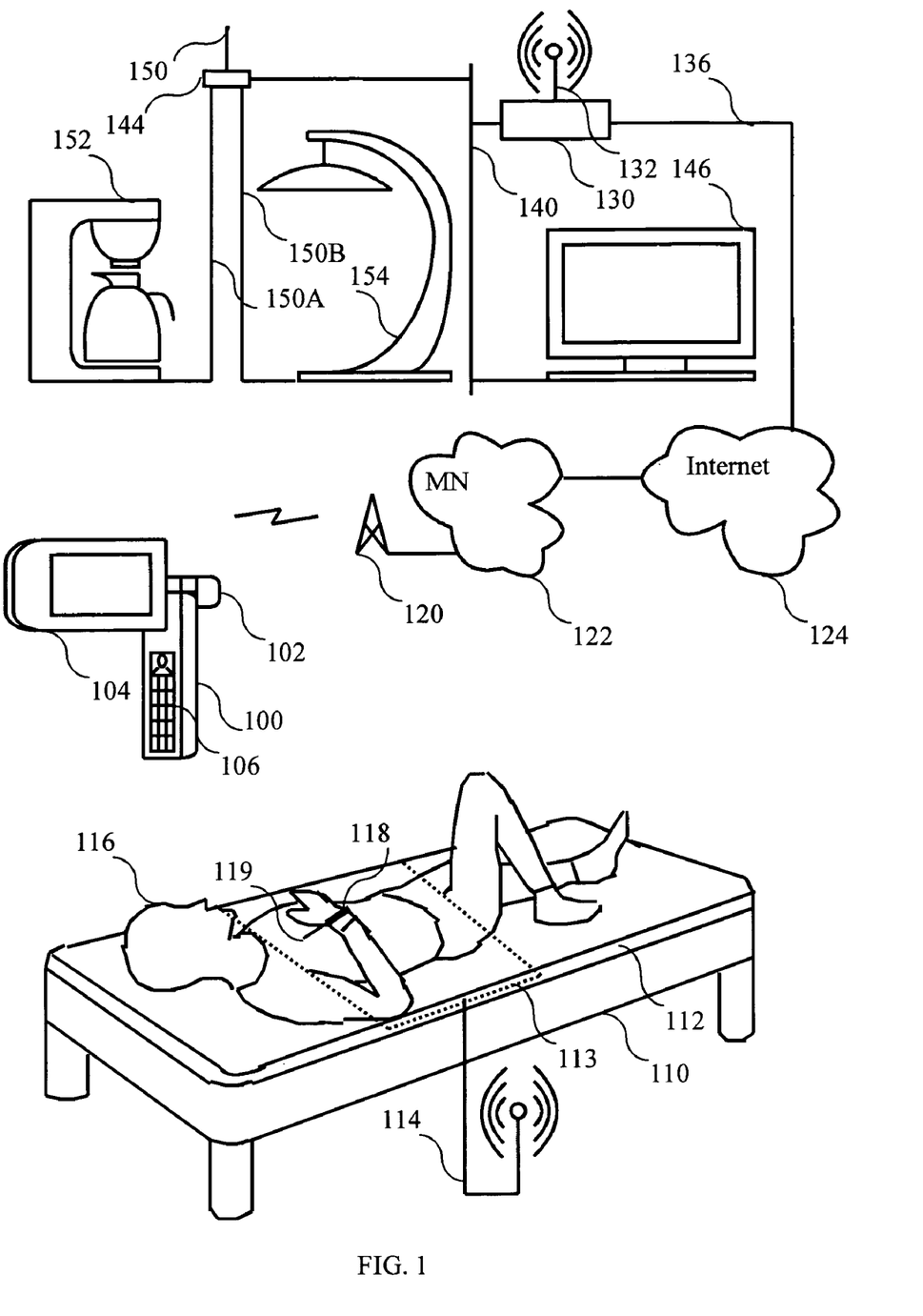
FIG. 1 illustrates a system for sleeper monitoring and domestic appliance control in one embodiment of the invention.

FIG. 1 is a block diagram illustrating a system for sleeper monitoring and domestic appliance control in one embodiment of the invention. In FIG. 1, which illustrates an embodiment of the invention there is illustrated in an abstract way a sleeper couched on a bed, a mobile terminal connecting via Internet to a system for controlling a number of household appliances. The components of the system are not illustrated in their actual sizes. In FIG. 1 there is illustrated a bed 110 on which there is placed a mattress 112 equipped with a pressure sensor 113. Alternatively, a separate pressure sensor may be placed on the mattress 112, inside or under a pillow, or under a bed-sheet. To pressure sensor 113 there is connected a first short-range radio transceiver 114. On mattress 112 there is illustrated a person 116. In one embodiment of the invention, the person may also wear a band 118 or any other device equipped with an accelerometer (not shown), for example, a pedometer (not shown) adjusted with a sleep analysis mode, and a second short-range radio transceiver 119. Pressure sensor 113 and band 118 communicate with a mobile terminal 100, which comprises a keypad 106, a display 104 and a camera 102. Mobile terminal 100 also comprises a third short-range radio transceiver (not shown), which is configured to communicate with first transceiver 114 and second transceiver 119. The third short-range radio transceiver may also be a mere receiver. Mobile terminal 100 communicates with a base station 120 within a mobile communication network 122. Mobile communication network 122 may, for example, comprise a Global System of Mobile communications (GSM) network, Universal Mobile Telecommunications System (UMTS) network, a Wireless Local Area Network (WLAN) or a General Packet Radio Service (GPRS). Mobile network 122 is configured to communicate with the Internet 124 or any other Internet Protocol (IP) network 124. Within the household or the accommodation of person 116 there is at least one computer, for example, a computer 130, which controls at least one domestic appliance. To computer 130 there is connected a visual entertainment center 146 and an electrical switch controller 144 via a local area network 140. Local area network 140 may also be a wireless network. Electrical switch controller 144 is configured to control power supply to a coffee maker 152 and a lamp 154. Electrical switch controller 144 is connected to a socket 150 and provides a socket for electrical cords 150A and 150B. Computer 130 is provided with an Internet connection 136 and a fourth short-range radio transceiver 132. Domestic appliances may also comprise, for example, air conditioning, warming, curtains and noise cancelling devices.

The first, the second, the third and the fourth transceiver may, for example, be a BLUETOOTH™ transceiver, an infrared transceiver, a WiMAX (Worldwide Interoperability for Microwave Access) transceiver, an UWB (Ultra Wide Band) transceiver, a WiBree transceiver or a wireless local area network transceiver. The first and the second transceivers may also be pure transmitters, whereas the third and the fourth transceivers may be pure receivers.

In one embodiment of the invention, mobile terminal 100 is configured to communicate directly with computer 130 via transceiver 132. In one embodiment of the invention, only band 118 is used to monitor the movements of person 116. In one embodiment of the invention, only pressure sensor 113 is used to monitor the movements of person 116. Thus, pressure sensor 113 and band 118 may be alternatives for the monitoring of movements. Band 118 may also be an ankle band or incorporated to the clothing of person 116.

In one embodiment of the invention, also the still or video camera 102 attached to the mobile terminal 100 may be used to monitor the movements of the person 116. The still or video camera 102 may take an image or short video file in certain intervals, such as e.g. 60 seconds, and differences in consecutive images are analyzed.

In one embodiment of the invention at least one household device comprises at least one computer such as computer 130, which is configured to communicate with mobile terminal 100 either directly via a short-range radio connection or via the Internet.

In one embodiment of the invention, at least one single electronic device is configured to communicate with mobile terminal 100 either directly via a short-range radio connection or via the Internet. These single electronic devices may be located in a hotel room, a cabin in a train or on a ship, etc.

In one embodiment of the invention, mobile terminal 100 comprises a radio receiver configured to receive at least one sleep sensor signal. There is also a microphone configured to receive ambient audio signals. The processor of mobile terminal 100 configured to execute a control entity, which is further configured determine a sleep state or a resting state of a user with the at least one sleep sensor signal, to determine a first disturbing noise pattern in said audio signals, to start the generating of at least one comfort audio pattern in order to alleviate subsequent disturbing noise patterns. Mobile terminal 100 may play the comfort audio patterns via its own loudspeakers or issue a remote control instruction to a remote household audio device such as stereos or a home entertainment center.

Disturbing factors that prevent a goo sleep, that is, a long and non-disturbed sleep, are numerous. Sources of disturbing factors are ranging from external sources. Traveling and changing place of sleeping introduce changes to the surrounding noises as well. Adoption to such changes is slow and at least takes several days before user cognitive system is adapted to a new type of surrounding noises. It is very true that getting good sleep is very difficult when place of the sleep is changed and part of the reasons belongs to the audio disturbing factors.

Still there are not yet simple and portable electronic solutions available to mass markets. The current embodiment of the invention provides an active mechanism which helps the cognitive system of the user to get easy adoption to sudden unpredictable audio disturbances and provides an easy way to get and extend the sleeping time. Our perception, notification and capability of detecting surrounding happenings are based on changes in time (new non observed effects exposed to the user). If changes are having repeated segments with relatively low sound level human cognitive system adopts and gets to stage without high attention (dormancy). Such stage helps in falling asleep easier.

Basic principle of the human cognitive and contemplation system is based on observing dynamical changes. Simply events which are containing not usual, not repeated and not "seen before" are catching user attention. Human cognitive system is easily activated by such events on the contrary these events will prevent humans from falling asleep. Similar principles are used for instance in audio-visual "eye-catching" effects in disco clubs or video-spots like moving/changing/ flashing images synchronized with sound, alternated lightning in public commercial billboards/advertisements and so on. When user sleeps sudden/accidental audio-visual happenings will bring cognition and perception system to aware stage and/or can prevent user to get to sleep. On the contrary it is well known that calm noise with uniform repeatability (like boring audio background) can help to get to sleep easier and faster.

In this embodiment there is presented a solution to exploit basic of human cognition principles and most carried piece of portable hardware (e.g. phone) to provide an advanced masking method of highly disturbed accidental noises over night. More precisely we propose to use a phone's audio hardware (microphone and speakers) and its processing system (software) to realize active system for elimination/suppression of audio disturbing factors in a portable form. Such system can mask disturbances and extend/improve users sleeping time and quality (Sleep Extender—SE). The system can operate completely automatic and user does not need to spend any attention over night. It is very suitable solution for travelers or people leaving in urbanized noisy areas or this suffering insomnia.

In one embodiment of the invention, the microphone in a mobile communication device can be utilized to monitor audio conditions in surrounding environment where user is sleeping. Relatively simple spectral analysis of the observed audio signals can be utilized to recognize accidental noises with certain frequency (F) that exceeds a certain notification level/threshold (Eth). Such accidental signals can have random or cyclic repeatability nature and presents Highly Disturbing Sound (HDS). In other words the HDS can be detected by a system integrate into a phone and analyzed by phone's dedicated software (SW). When the HDS are detected the ES system will react instantaneously and start emitting appropriate Low Disturbing Sound (LDS). Such LDS will be perceived by the sleeper's cognitive system (via ears, brain etc.) and "mask" the HDS and suppress influence of the highly disturbing sources to the user sleep state. Once the HDS is detected the level of the LDS will be slowly introduced to the sleeper atmosphere to an adequate masking level (L), which is sufficient for masking the HDS. Furthermore the level L is dynamically adjusted in accordance with the type and level of the detected HDS. The LDS presents uniform "boring" audio composition with relatively low level but sufficient to overcome the disturbances by the HDS. Several types of LDS patterns are recommended such: Waterfall/ Running water sound, for example, from pipes or spring; Rain/Shower/Downfall sound; Sea wave's sound; Wind sound; Wind in forest e.g. sound made by leaves on trees. Alternatively user can record his/her favorite LDS pattern which can be used also to dynamically lower influences of the HDS. The ES system presents completely automatic solution which works independently of user and which dynamically masks/hide the HDS disturbing factors from the user cognition system. Furthermore the ES system can be used prior sleeping e.g. to get to sleep on an easier way. For in stance if user has high "metal pressure" (by daily overstresses) he/she can select an "Easy sleep mode" which will just activate the LDS profile to slow down users cognitive systems and speed up time to get to sleeping stage.

In one embodiment of the invention, the user keeps his phone in the proximity where she is sleeping, for example, in the same room, hotel room, train and so on. Before going to sleep the user activates the "Sleep Extender" service at phone. The phone's microphone starts monitoring the sleeping environment and the SW starts actively analyzing the HDS disturbing factors, if any. When and if the HDS goes over certain level the phone activate the speakers and starts slowly introducing LDS masking sound profile to a level which will mask the HDS sound. Notice that introduction of the LDS is made slowly to give to user certain period of time to adopt and to prevent awaking just by the LDS itself. The system keeps running the LDS until the HDS signals are observed within certain period of time and continues emitting for a while even if there are not the HDS. Once the HD disappear completely the volume the LDS goes slowly down and finally disappear completely until the next HD appears. Such automatic functional device can extend users sleeping time in noisy mornings in unpredictable nosy neighborhoods and in highly urbanized areas.

Figure 2:
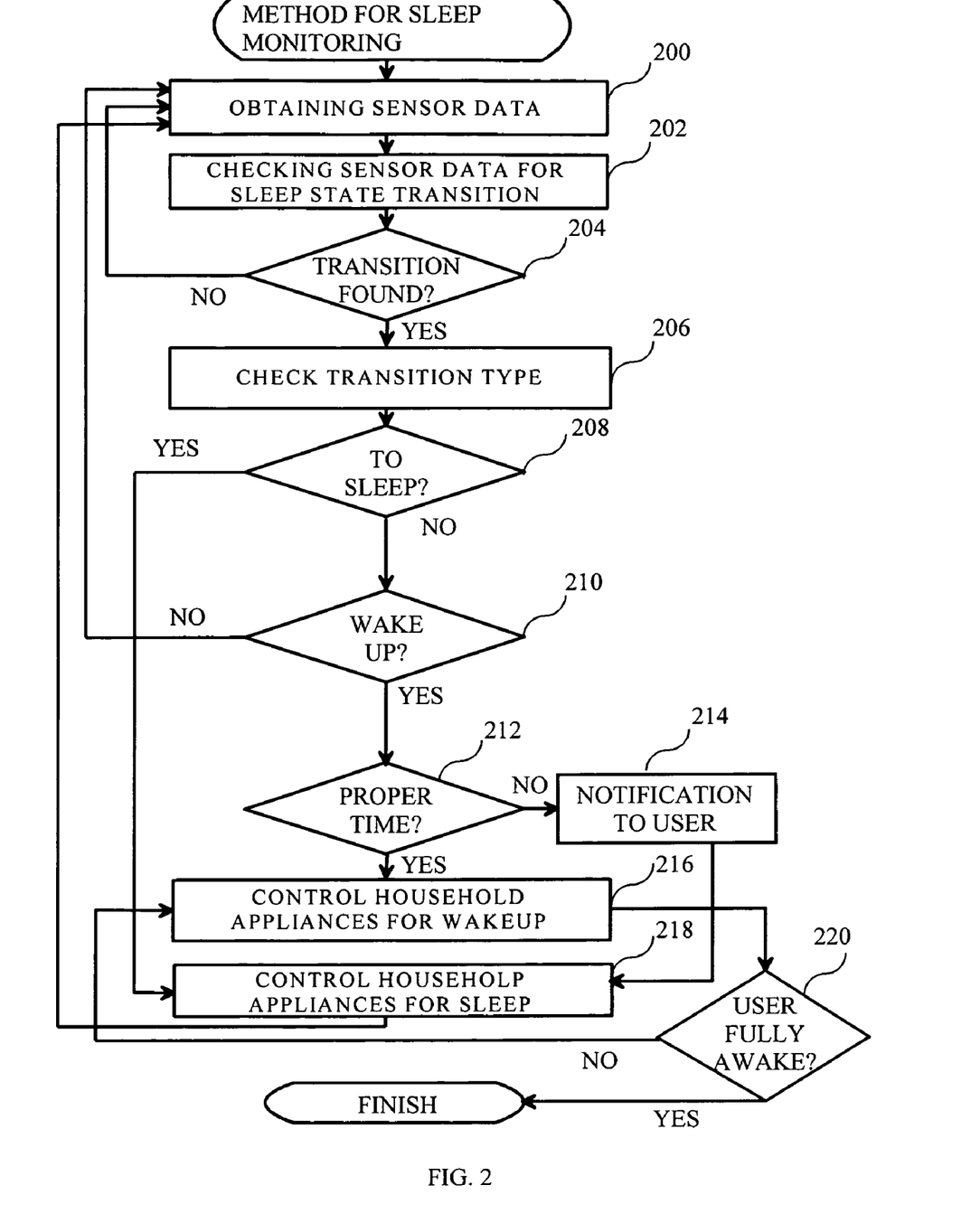
FIG. 2 is a flow chart illustrating a method for sleeper monitoring in one embodiment of the invention.

FIG. 2 is a flow chart illustrating a method for sleeper monitoring in one embodiment of the invention.

At step 200, sensor data is obtained to a mobile terminal from at least one sensor. The at least one sensor comprise, for example, a pressure sensor adapted to be placed under a sleeper, a pressure sensor incorporated to the sleepers clothing and an accelerometer worn by the sleeper. The at least one sensor is configured to detect the sleepers movements and to provide the movement data via a short-range radio to the mobile terminal. The movement data received to the mobile terminal is furnished with time data either in the mobile terminal or by the at least one sensor. Using a pressure sensor, the movements may be determined on several levels, namely, those of limb and body movement, respiration and pulse. A change in the respiration rate may indicate falling asleep.

At step 202, the movement data is analyzed by the mobile terminal in order to determine a transition in and/or a condition of the sleepers sleep. The movement data is analyzed for a predefined time, for example, two minutes to determine a change in the sleep phase. Possible transitions comprise falling asleep, waking up, entering the REM phase, entering the delta phase, exiting the delta phase for REM phase or vice versa. The exiting the delta phase for REM phase may be detected, for example, by determining an increase in the sleepers motions after a relatively still phase.

At step 204, it is checked by the mobile terminal whether a transition may be determined to take place. If no transition is detected, the method continues at step 200. Otherwise, the method continues at step 206.

At step 206, the transition type is checked.

At step 208, it is determined if the transition is from the awake state to falling asleep. If the transition is from awake to asleep, the method continues at step 218. Otherwise, the method continues at step 210.

At step 210, it is determined if the transition is from the delta phase to the REM phase or from the REM phase to awake state. If such a transition takes place, the method continues at step 212. Otherwise, the method continues at step 200.

At step 212, it is determined if the sleeper may be woken up. The determination may also use a wakeup time window defined by the user of the mobile terminal. If it is determined that the time for wakeup is proper, the method continues at step 216. Otherwise, the method continues at step 214.

In one embodiment of the invention, the user is allowed to remain in the REM phase at least a predefined period within the boundary permitted by a user defined time window.

At step 214, an optional notification may be given to the user. The notification is only given, if the transition determined at step 210 is to awake. The notification is, for example, an audio notification stating that the user may continue to sleep. The audio notification may indicate how much time remains until wakeup. Thereupon, the method continues at step 218.

At step 216, at least one household appliance is controlled by the mobile terminal in response to the wakeup. For example, a coffee maker may be powered on. Similarly, a radio or a television may be switched on. The mobile terminal may communicate with a home personal computer, which controls the household appliances at the request of mobile terminal. The controlling of the household appliances may be performed directly via a short-range radio connection between the mobile terminal and the personal computer or via the Internet and an Internet connection to the personal computer. The mobile terminal may also start playing a tune.

At step 218, the mobile terminal removes disturbing factors to avoid disturbing the user's sleep. The mobile terminal may control at least one household appliance, for example, request a television to be switched off and request light to be switched off or smoothed. Alternatively, at step 218, the mobile terminal adjusts and maintains at least one factor and at least one household appliance that deepen or stabilize the user's sleep. For example, disturbing outside noises may be compensated with a comfort noise or noise cancellation, if the sleeper wears headsets. As a further example, electrically controlled curtains may be closed in order to block sunshine through the windows.

At step 220, it is checked if the user is fully awake. If the user is fully awake, the method is finished. If the user is not fully awake, the method continues at step 216.

Figure 3:
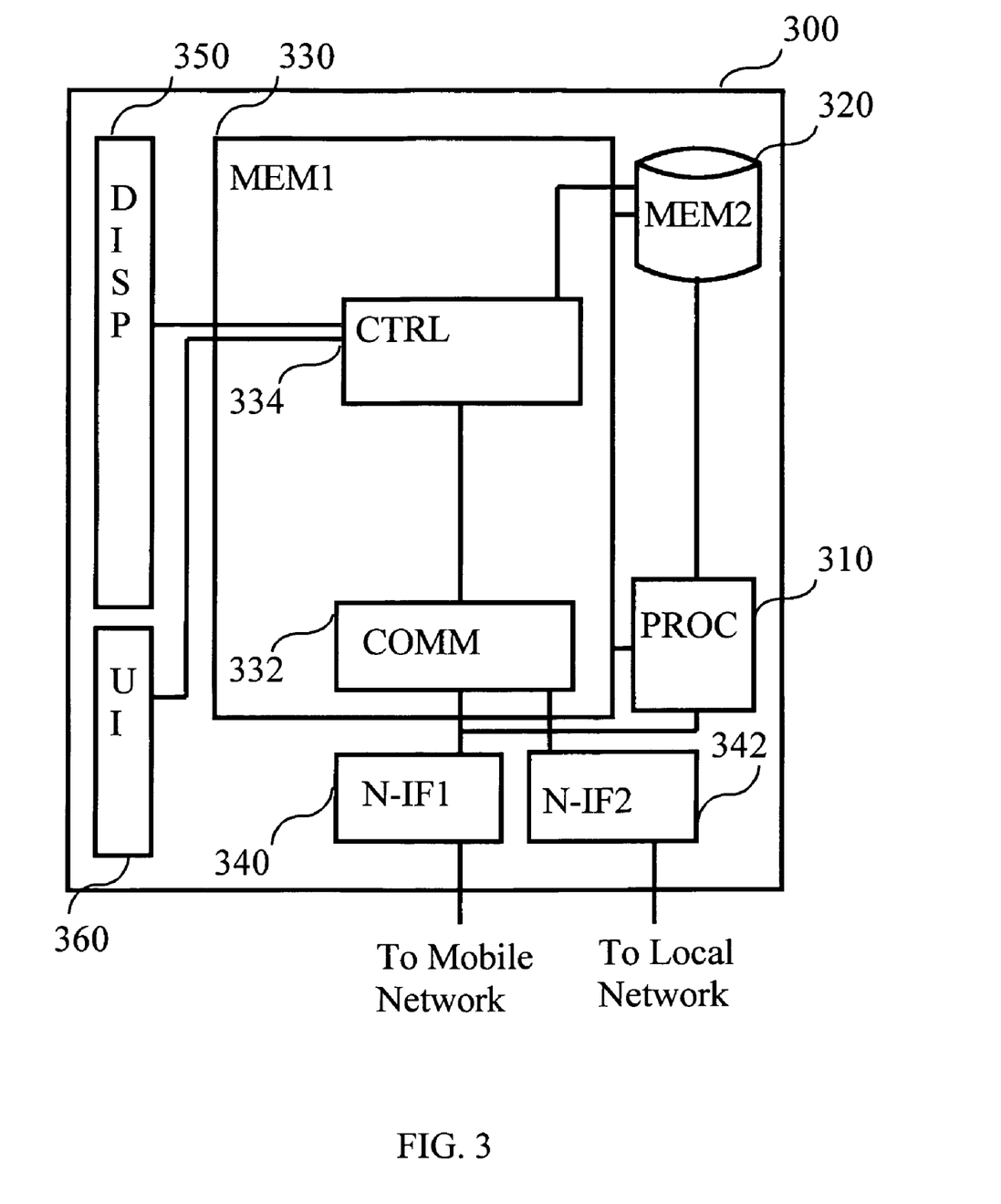
FIG. 3 is a block diagram illustrating an electronic device in one embodiment of the invention.

FIG. 3 is a block diagram illustrating an electronic device in one embodiment of the invention. In FIG. 3 there is illustrated an electronic device 300. Electronic device 300 comprises a processor 310, a secondary memory 320, a primary memory 330, a display 350, a user interface 360 and a camera unit 370. User interface 360 may also comprise a loudspeaker and a wakeup function, which may play a wakeup signal or melody. The wakeup function may also comprise a vibration alerting unit. User interface 360 may also comprise a microphone (not shown). Electronic device 300 may also comprise any number of other processors and any number secondary memory units. There may also be other primary memories with separate address spaces. Electronic device 300 comprises also a first network interface 340. The first network interface may, for example, be a cellular radio interface, a Wireless Local Area Network (WLAN) interface, a local area network interface or a wide area network interface. The first network interface is used to communicate to the Internet or locally to a at least one personal computer, which controls at least one household appliance. Electronic device 300 comprises also a second network interface 342. The second network interface may, for example, be a Wireless Local Area Network (WLAN) interface, a short-range radio interface, a BLUETOOTH™ interface, an infrared interface or a local area network interface. The second network interface is used to obtain information from at least one sleep sensor.

Processor 310 executes a number of software entities stored at least partly in primary memory 530. Primary memory 330 comprises a communication entity 332 and a sleep monitoring and household appliance control entity, in other words, a control entity 334. Communication entity 332 communicates with remote network nodes for enabling them to communicate with other entities within electronic device 300. Communication entity 332 comprises, for example, the Internet Protocol (IP) protocol stack.

The entities within electronic device 300 such as communication entity 332 and control entity 334 may be implemented in a variety of ways. They may be implemented as processes executed under the native operating system of the network node or the electronic device. The entities may be implemented as separate processes or threads or so that a number of different entities are implemented by means of one process or thread. A process or a thread may be the instance of a program block comprising a number of routines, that is, for example, procedures and functions. The entities may be implemented as separate computer programs or as a single computer program comprising several routines or functions implementing the entities. The program blocks are stored on at least one computer readable medium such as, for example, a memory circuit, a memory card, a holographic memory, magnetic or optic disk. Some entities may be implemented as program modules linked to another entity. The entities in FIG. 3 may also be stored in separate memories and executed by separate processors, which communicate, for example, via a message bus or an internal network within the network node or the electronic device. An example of such a message bus is the Peripheral Component Interconnect (PCI) bus. The internal network may be, for example, a local area network. The entities may also be partly or entirely implemented as hardware, such as ASICS or FPGAs.

It is obvious to a person skilled in the art that with the advancement of technology, the basic idea of the invention may be implemented in various ways. The invention and its embodiments are thus not limited to the examples described above; instead they may vary within the scope of the claims.

The invention claimed is:

1. A method comprising:
    causing, at least in part, data relating to movement of a sleeper to be received at a mobile communication device from one or more sensors;
    analyzing the data over a predetermined interval to determine a transition in sleep state of the sleeper;
    generating, based on the transition, at least one control signal;
    causing, at least in part, the at least one control signal to be transmitted to one or more electronic devices and causing, at least in part, a condition of an environment of the sleeper to be detected, wherein the transition relates to the sleeper falling more or less asleep, and the at least one control signal is generated to cause the one or more electronic devices to stop or diminish the condition.

2. The method according to claim 1, wherein the transition relates to the sleeper falling less asleep, the method further comprising:
    determining whether the sleeper may be woken,
    wherein the at least one control signal is generated to cause the at least one electronic device to start or increase one or more functions of the one or more electronic devices.

3. The method according to claim 1, wherein the transition relates to the sleeper falling more asleep, the at least one control signal being generated to cause the one or more electronic devices to continue producing one or more soporific effects.

4. The method according to claim 1, wherein the transition is to a rapid eye movement sleep state, the method further comprising:
    determining a time window for waking the sleeper; and
    causing, at least in part, a duration of the rapid eye movement sleep state to be monitored;
    wherein a wakeup function of the mobile communication device is caused, at least in part, to be delayed until the duration is equal to a predetermined duration or caused, at least in part, to be initiated if the time window is exhausted before the duration is equal to the predetermined duration.

5. The method according to claim 1, the method further comprising:
    determining a sleep state of the sleeper;
    determining a time window for waking the sleeper; and
    causing, at least in part, a wakeup function of the mobile communication device to be adjusted based on the sleep state.

6. The method according to claim 1, wherein at least one of the one or more electronic devices comprises a domestic appliance.

7. The method according to claim 1, wherein the one or more electronic devices comprise at least one of a lighting control device, a radio, a media center, an air conditioning system, and a noise cancellation device.

8. The method according to claim 1, wherein at least one of the one or more sensors comprises an accelerometer configured to detect the movement of the sleeper.

9. The method according to claim 8, wherein the data is caused, at least in part, to be received via a short-range radio connection.

10. The method according to claim 8, wherein the accelerometer is included as part of a wearable band.

11. The method according to claim 8, wherein at least one of the one or more sensors comprises a pressure sensor configured to detect movement of the sleeper.

12. The method according to claim 11, wherein the pressure sensor is configured to receive one or more tapping control signals.

13. The method according to claim 12, wherein the tapping control signals are configured to facilitate the transition.

14. An apparatus comprising:
    at least one processor; and
    at least one memory including computer program code, the at least one memory and the computer program code being configured, with the at least one processor, to cause the apparatus at least to:
        receive data relating to movement of a sleeper from one or more sensors,
        analyze the data over a predetermined interval to determine a transition in sleep state of the sleeper,
        generate, based on the transition, at least one control signal,
        transmit the at least one control signal to one or more electronic devices and detect a condition of an environment of the sleeper, wherein the transition relates to the sleeper falling more or less asleep, and the at least one control signal is generated to cause the one or more electronic devices to stop or diminish the condition.

15. The apparatus according to claim 14, wherein the transition relates to the sleeper falling less asleep and the at least one memory and the computer program code are further configured, with the at least one processor, to cause the apparatus at least to:
    determine whether the sleeper may be woken,
    wherein the at least one control signal is generated to cause the at least one electronic device to start or increase one or more functions of the one or more electronic devices.

16. The apparatus according to claim 14, wherein the transition relates to the sleeper falling more asleep, the at least one control signal being generated to cause the one or more electronic devices to continue producing one or more soporific effects.

17. The apparatus according to claim 14, wherein the transition is to a rapid eye movement sleep state and the at least one memory and the computer program code are further configured, with the at least one processor, to cause the apparatus at least to:
    determine a time window for waking the sleeper; and
    monitor a duration of the rapid eye movement sleep state,
    wherein a wakeup function of the apparatus is delayed until the duration is equal to a predetermined duration or initiated if the time window is exhausted before the duration is equal to the predetermined duration.

18. The apparatus according to claim 14, wherein the at least one memory and the computer program code are further configured, with the at least one processor, to cause the apparatus at least to:
  determine a sleep state of the sleeper;
  determine a time window for waking the sleeper; and
  adjust a wakeup function of the apparatus based on the sleep state.

19. The apparatus according to claim 14, wherein the at least one memory and the computer program code are further configured, with the at least one processor, to cause the apparatus at least to:
  receive the data over a short-range radio connection; and
  transmit the one or more control signals over a radio connection.

20. The method according to claim 1, wherein the movement of the sleeper relates to movement of a limb of the sleeper or movement of a body of the sleeper.

21. The method according to claim 1, wherein the transition relates to a determination of an increase in motion of the sleeper subsequent to a determination of a relatively still phase of the sleeper.

22. The apparatus according to claim 14, wherein at least one of the one or more electronic devices comprises a domestic appliance.

23. The apparatus according to claim 14, wherein the one or more electronic devices comprise at least one of a lighting control device, a radio, a media center, an air conditioning system, and a noise cancellation device.

24. The apparatus according to claim 14, wherein at least one of the one or more sensors comprises an accelerometer configured to detect the movement of the sleeper.

25. The apparatus according to claim 22, wherein the accelerometer is included as part of a wearable band.

26. The apparatus according to claim 22, wherein at least one of the one or more sensors comprises a pressure sensor configured to detect movement of the sleeper.

27. The apparatus according to claim 26, wherein the pressure sensor is configured to receive one or more tapping control signals.

28. The apparatus according to claim 25, wherein the tapping control signals are configured to facilitate the transition.

29. The apparatus according to claim 14, wherein the apparatus is a mobile communication device.

30. The apparatus according to claim 14, wherein the movement of the sleeper relates to movement of a limb of the sleeper or movement of a body of the sleeper.

31. The apparatus according to claim 14, wherein the transition relates to a determination of an increase in motion of the sleeper subsequent to a determination of a relatively still phase of the sleeper.

* * * * *